United States Patent [19]

Romeo et al.

[11] Patent Number: 5,538,730
[45] Date of Patent: Jul. 23, 1996

[54] CARBOXYLIC POLYSACCHARIDE DERIVATIVES

[75] Inventors: Aurelio Romeo, Rome; Gino Toffano; Lanfranco Callegaro, both of Padua, all of Italy

[73] Assignee: Fidia S.p.A., Abano Terme, Italy

[21] Appl. No.: 216,858

[22] Filed: Mar. 24, 1994

Related U.S. Application Data

[63] Continuation of Ser. No. 944,231, Sep. 14, 1992, abandoned.

[30] Foreign Application Priority Data

Sep. 13, 1991 [IT] Italy ................... PD91A0160

[51] Int. Cl.⁶ ............... A61K 47/38; A61K 9/00
[52] U.S. Cl. .................. 424/401; 424/423/443; 536/20
[58] Field of Search ............... 536/20; 424/401, 424/423, 443

[56] References Cited

U.S. PATENT DOCUMENTS

| | | | |
|---|---|---|---|
| 4,528,283 | 7/1985 | Lang et al. | 514/55 |
| 5,122,598 | 6/1992 | della Valle et al. | 536/20 |

FOREIGN PATENT DOCUMENTS

| | | |
|---|---|---|
| 0161212 | 11/1985 | European Pat. Off. . |
| 0216453 | 1/1987 | European Pat. Off. . |
| 0342557 | 11/1989 | European Pat. Off. . |

OTHER PUBLICATIONS

J. P. Sachetto *Seifen, Ole, Fette, Wachse*, vol. 113, No. 8 (May 1987) pp. 266–267.

Plisko et al Russian Chemical Reviews 46(8) 1977 pp. 1470–1487.

Horton et al Carbohydrate Research 29(1973) 173–179.

"Le Chitosane" by Patrick Broussignac Chimie et industrie–Genie Chimique, vol. 99, No. 9 (1968) pp. 1241–1247.

D. Horton et al Carbohydrate Research, vol. 29 (1973) pp. 173–179.

E. A. Plisko et al Russian Chemical Reviews, vol. 46, No. 8 (1977) pp. 764–774.

*Primary Examiner*—Peter F. Kulkosky
*Attorney, Agent, or Firm*—Birch, Stewart, Kolasch & Birch

[57] ABSTRACT

Copolymers of the formula:

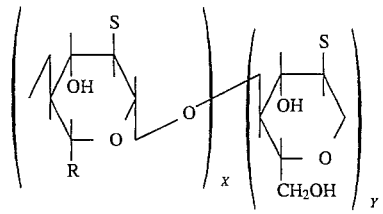

wherein the bonds between the glucoside units are $\beta$ (1→4), the degree of polymerization referred to a single glucoside unit varies from about 50 to 50,000, R is a free or esterified carboxy group and S is an amino or acylamino group. The part designated by x may vary between about 5% and 100% and that designated by y may vary between about 95% and 0%. At least a part of the R groups are esterified carboxy groups, and at least a part of the S groups are acylamino groups. Salts of these copolymers are also disclosed. The products of the invention are particularly useful in the cosmetic field.

26 Claims, No Drawings

CARBOXYLIC POLYSACCHARIDE DERIVATIVES

This application is a continuation of application Ser. No. 07/944,231 filed on Sep. 14, 1992, now abandoned.

SUMMARY OF THE INVENTION

The present invention is directed to novel carboxylic esters of a polysaccharide constituted by units of 2-amino-2-deoxy-glucuronic acid and glucosamine and their N-acyl derivatives. This polysaccharide is a derivative of chitosan (that is, chitin completely or partially deacetylated at the aminic nitrogen) and is obtained by oxidation of the primary alcoholic groups and carboxylic groups, preferably to an extent varying between 20% and 90%, and subsequent optional acylation of the amino groups present in the 2-position.

These esters possess properties similar to those of other known mucopolysaccharides such as hyaluronic acid and its esters, chitins and chitosans and they can be applied in all corresponding industrial sectors.

The esters according to the present invention include total and partial esters. The unesterified carboxy groups in the partial esters can be salified with metals or organic bases, and such salts form part of the present invention; also included in the invention are salts obtained by acid addition to the free amino groups that may be present.

The present invention is also directed to the use of the novel esters in various fields, but mainly in cosmetics and surgery, industrial articles and especially bioplastic articles made with them, and the cosmetic compositions containing them. Moreover, the invention includes the methods for the preparation of said esters.

Chitosan is a polysaccharide constituted by units of glucosamine and/or acetylglucosamine bound together by a glucoside bond β(1→4). It can be obtained from chitin by partial or total deacylation of the acetylamino groups in the 2-position by alkaline hydrolysis, as has been amply described in the literature ("Le Chitosane" by Patrick Broussignac CHIMIE ET INDUSTRIE-GENIE CHIMIQUE, Vol. 99, No. 9, May 1968; Carbohydrate Research 29, 173, 1973). The polysaccharide at the base of the new esters of the present invention is a chitosan, partially or totally oxidized at the carbinol groups and partially or totally acylated at the amino groups. The new products of the present invention are more precisely composed of the following formula (I):

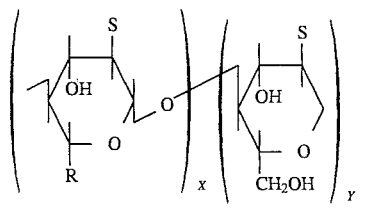

the bonds being β(1→4) between the glucoside units, wherein the degree of polymerization, referred to a single glucoside unit, varies between values of about 50 and 50,000, R is a free or esterified carboxy group with an alcohol of the aliphatic, araliphatic or alicyclic series with a maximum of 26 carbon atoms and S represents an amino or acylamino group wherein the acyl group is derived from an acid chosen from the group formed by:

an aliphatic acid with a maximum of 26 carbon atoms an araliphatic acid with only one benzene residue and wherein the aliphatic chain has a maximum of 4 carbon atoms and an aromatic acid with only one benzene ring. The x and y indicate the percentage of the number of molecules of the respective formulae. The successive order of the single glucoside derivatives may vary, and x may vary between about 5% and 100%, and y may vary between 95% and 0%. At least a part of the R groups are esterified carboxy groups, and at least a part of the S groups are acylamino groups.

The invention also includes salts of these molecules, these salts being metal salts or salts formed with organic bases at the carboxy groups or salts obtained by acid addition at the free amino groups.

According to the above definition, the S group in the compounds of said formula (I) represents an acylamino group or an amino group that is free or possibly salified with acids.

The acyl groups which acylate the amino groups may have the same or different glucoside units as each other. Particularly important are the compounds of formula (I) wherein 100% of the S groups are acylamino groups or wherein a part, preferably varying between 95% and 25%, is constituted by amino acylated groups and another part, preferably varying between 5% and 70% is constituted by amino groups that are free or salified by salts obtained by acid addition. Particularly important are the derivatives wherein a certain aliquot, preferably varying between 10% and 60% of these acyl groups is constituted by acyl groups derived from higher homologues of acetic acid or by one of said aromatic or araliphatic acids, and the other part, preferably varying between 90% and 40%, of the acyl groups, is derived from acetic acid.

Alcohols of the aliphatic series to be used preferably as esterifying components of the carboxy groups of the compounds of formula (I) according to the present invention are those having a maximum of 12 carbon atoms, which may be saturated or unsaturated and which may optionally be substituted by halogens or by other free or functionally modified groups, such as amino or hydroxy groups. Alcohols of this type preferred for use according to the present invention are those with a maximum of 4 carbon atoms. Among these alcohols, special mention should be made of those which are saturated and unsubstituted, such as methyl, ethyl, propyl, isopropyl alcohols, n-butyl alcohol, isobutyl alcohol, and tert-butyl alcohol. Examples to be cited of alcohols with a greater number of carbon atoms are amyl, hexyl, octyl, nonyl and dodecyl alcohols, especially those with a linear chain, such as n-octyl and n-docecyl alcohol. Of the substituted alcohols of these groups, bivalent alcohols should be mentioned, such as ethylene glycol, propylene glycol and butylene glycol, trivalent alcohols such as glycerine, amino alcohols such as aminoethanol, aminopropanol, n-aminobutanol and their derivatives, dimethylated and diethylated in the amino function, and choline. Lower, unsaturated alcohols to be considered are allyl alcohol and propargyl alcohol. Especially important for the purposes of the present invention are unsaturated, higher alcohols with one or two double bonds, such as those contained in many essential oils and with an affinity for terpenes such as citronellol, geraniol, nerol, and linalol. Alcohols of the araliphatic series to receive special mention are those with only one benzene residue and wherein the aliphatic chain has a maximum of 4 carbon atoms and wherein the benzene residue may be substituted by 1 to 3 methyl or hydroxy groups or by halogen atoms, especially chlorine, bromine or fluorine, and wherein the aliphatic chain may be substituted by one or more functions chosen from the group constituted by free or mono- or dimethylated amino groups or by pyrrolidine or piperidine groups. Among these alcohols should be mentioned especially benzyl alcohol, phenethyl alcohol, 2-fluoro-benzyl alcohol, and 3-chloro-benzyl alcohol.

The alcohols of the cycloaliphatic or aliphatic-cycloaliphatic series may derive from mono- or polycyclic hydrocarbons. Among the alcohols derived from single-ringed, cyclic hydrocarbons, special mention should be made of those having a maximum of 12 carbon atoms, the rings having preferably between 5 and 7 carbon atoms, which may be substituted for example, by one to three lower alkyl groups, such as methyl, ethyl, propyl or isopropyl groups. Specific alcohols of this group are, for example, cyclohexanol, cyclohexanediol, cyclohexane-1,2,3-triol and cyclohexane-1,3,5-triol (fluoroglucite), inositol, and alcohols which are derived from p-menthane, such as carbomenthol, menthol, $\alpha$- and $\gamma$-terpineol, terpineol-1, terpineol-4 and piperitol, or the mixture of these alcohols known as "terpineol" and 1,4- and 1,8-terpinol. Examples of alcohols derived from hydrocarbons with condensed rings, for example those of the thujane, pinane or canfane groups, include thujanol, sabinol, pinol hydrate, D-and L-borneol and D-and L-isoborneol.

The N-acyl group in the compounds of said formula (I), derived from an aliphatic acid with a maximum of 26 carbon atoms, is preferably a group of a saturated acid having a maximum of 12 carbon atoms. Among the acyl moieties of this group, particularly important are those derived from the following specific acids: formic, acetic, propionic, n-butyric, n-isobutyric, n-valerianic, isovalerianic, trimethylacetic, capronic, caprilic, caprinic, undecylic, lauric, palmitic and stearic. Among the acyl groups derived from the unsaturated acids, particularly important are those derived from higher acids having from 18 to 22 carbon atoms, such as oleic acid, erucic acid, and bassidic acid. These acids can also be substituted by functional groups, for example, hydroxy, alkoxy or phenoxy groups or by halogens. Among these acids special mention should be made of phenoxyacetic acid.

Among the araliphatic acids should be mentioned above all those with only one benzene ring, optionally substituted by 1 to 3 methyl or methoxy groups or by halogen atoms, preferably F, Br and Cl, and wherein the aliphatic chain has a maximum of 4 carbon atoms and can be straight or ramified, saturated or unsaturated. Among these acids there should be preferably mentioned: phenylacetic acid, 2-phenylpropionic acid, 3-phenylpropionic acid, cinnamic acid, 2-phenylbutyric acid, 3-phenylbutyric acid, 4-phenylbutyric acid, 4-fluorophenylacetic acid, the 3 isomers of toluylacetic acid, and 3,4,5-trimethoxy cinnamic acid.

The aromatic acyl groups are derived, according to the above definition, from acids with only one benzene ring. This ring can be substituted by one to three groups chosen from methyl, methoxy, and methylenedioxylic groups and halogen atoms, preferably F, Cl and Br. Among said acids should be mentioned benzoic acid, anisic acids, dimethoxybenzoic acids, in particular veratric acid, the trimethoxybenzoic acids, such as asaronic acid, toluic acids, 2-chlorobenzoic acid, 4-chlorobenzoic acid, 4-fluorobenzoic acid, 3,5-dichlorobenzoic acid, and piperonyl acid.

The degree of polymerization n of the compounds of formula (I) varies between values of about 50 and about 50,000. Particularly important are the esters of formula (I) in which the degree of polymerization n falls between values of about 240 to about 2,400. In the compounds of formula (I), x corresponds preferably to a percentage varying between 20 and 90% and especially between 50 and 90%.

In the partial esters according to the invention, the percentage of the esterifying groups may vary widely according to the use to which the product is to be put, and this mainly concerns uses in the various fields of application. The degree of esterification of the compounds of formula (I) with said alcohols depends first of all on the special properties to be obtained, for example, greater or lesser lipophilic or hydrophilic characteristics, for instance in cosmetics with regard to certain tissues, such as the skin. Generally, a high degree of esterification, up to total esterification, increases the product's lipophilic characteristics and therefore diminishes water solubility. Naturally, the molecular weight of the same esterifying component must be borne in mind, as this usually influences water solubility in an inversely proportional manner.

Of particular interest are partial esters in which at least 5% and at the most 90% of all the carboxy groups are esterified, and especially those with a percentage of esterification of between 50 and 80%.

In the partial esters of the invention the unesterified carboxy groups can be kept free or they can be salified. For the formation of said salts, the bases are chosen according to the use to which the product is to be put. It is possible to form inorganic salts derived from alkaline metals, such as potassium and especially sodium and ammonium, or derived from alkaline earth metals, such as calcium or magnesium salts or aluminum salts. Of particular interest are the salts with organic bases, especially azotated bases and therefore aliphatic, araliphatic, cycloaliphatic or heterocyclic amines, especially cosmetically acceptable bases. Aliphatic amines are to be considered for many uses, for example, mono-, di-, and trialkylamines with alkyl groups having a maximum of 8 carbon atoms or arylalkylamines with the same number of carbon atoms in the aliphatic part and where aryl means a benzene group, optionally substituted by 1 to 3 methyl groups or halogen atoms, or hydroxy groups. The bases for the formation of salts can also be cyclic such as monocyclic alkyleneamines with cycles of between 4 and 6 carbon atoms, optionally interrupted in the cycle by heteroatoms chosen from the group formed by nitrogen, oxygen and sulphur, such as piperidine, morpholine or piperazine. Alternatively, they may be substituted, for example, by amino or hydroxy functions, such as aminoethanol, ethylene diamine, ephedrine or choline. It is also possible to form quaternary ammonium salts of the partial esters, for example, tetraalkylammonium salts and preferably salts of this kind wherein the fourth alkyl group has between 1 and 4 carbon atoms, for example, a methyl group.

The compounds of formula (I) according to the invention which have free amino groups can be used also in the form of salts obtained by acid addition. Among the acids which can provide such salts, should be mentioned in particular hydracids, such as hydrochloric acid, bromhydric acid, phosphoric acid, sulphuric acid, lower aliphatic acids having a maximum of 7 carbon atoms such as formic acid, acetic or propionic acid, succinic or maleic acid.

Chitin, chitosan and their derivatives have been studied with the objective of using them in various branches of industry and in medicine ("Chitin and its chemical transformations" Plisko, et al., RUSSIAN CHEMICAL REVIEWS, 4, (8), 1977). These studies revealed the ability of these substances to form fibers and films that can be added to tissues and paper to improve their mechanical characteristics and the fixing of inks and dyes, as well as their use as ion exchangers. Because of their low toxicity, even at high doses, it was possible to demonstrate in numerous studies that they are able to inhibit or activate some enzymes, including pepsin, lipase, deoxyribonuclease, hyaluronidase and glucuronidase, and that their sulfonates present the same properties as heparin.

Attempts have been made to use chitin in almost all sectors of industry. The use of chitin has been suggested in the mining industry, in glass staining and synthetic material dyeing, and in the cosmetic and food industries. It has been considered for use in water purification. Chitin has also been oxidized using various agents such as chromic anhydride and nitrogen oxides, to give products in which a part of the primary carbonylic groups are transformed into carboxy groups. These products, described for example in European patent application No. 0161212 by Battelle Memorial Institute, have properties very similar to those of hyaluronic acid and its derivatives, and their use has been proposed in cosmetics as skin moisturizers.

It has now been discovered, within the scope of the present invention, that the new products of formula (I) not only have similar properties to chitin, chitosan and oxidized chitins, but that they are also extremely suitable, unlike the above-named known products, for the formation of threads and sheets and that they can be used to obtain various bioplastic articles such as films, sheets, gauzes, bandages, threads and tissues, for use as sanitary and surgical articles. As the new esters of formula (I) have analogous properties to hyaluronic acids and their esters, they can also be used in some industrial sectors where these materials are used, for example, as additives for various polymeric materials used for sanitary and surgical articles such as polyurethanes, polyesters, polyolefins, polyamides, polysiloxanes, vinylic and acrylic polymers and carbon fibers. Moreover, it is possible to manufacture directly biocompatible sanitary and medical articles, insoluble in physiological solutions, of any form whatsoever, such as heart valves, intraocular lenses, vascular clips, pacemakers and other similar articles. Such articles can be obtained advantageously from appropriate organic solutions of the new compounds of formula (I), which lend themselves to the formation of threads and sheets in order, to obtain films, sheets and threads to be used for example in surgery, such as supports and replacements of the skin in cases of serious damage to the skin, for example in the case of burns, or as suture threads in surgery.

The organic solvent used for the above-described solutions is, for example, a ketone, an ester or an aprotic solvent such as an amide of a carboxylic acid, especially a dialkylamide of an aliphatic acid having between 1 and 5 carbon atoms. The organic solvent is especially an organic sulfoxide, that is, a dialkylsulfoxide with alkyl groups having a maximum of 6 carbon atoms, such as especially dimethylsulfoxide or diethylsulfoxide. The solution undergoes lamination or spinning, and the organic solvent is removed by contact with another organic or aqueous solvent which can be mixed with the first solvent and wherein the compound of formula (I) is not soluble, especially a lower aliphatic alcohol, for example ethyl alcohol.

The esters according to the present invention have hydrating and lubricating properties similar to those of the oxidized chitins of the aforesaid European patent No. 0161212, but they present notable advantages over these materials because of their use in cosmetics, due to the possibility of regulating within wide limits and possibly increasing their moisturizing and lubricating potential. It is also possible to obtain, where necessary, excellent "retard" effects with the products of the present invention.

Because of these properties, the new products according to the invention can be used to advantage in cosmetics and also in dermatology.

The new compounds of formula (I) can play two different roles in cosmetics: they can represent the cosmetic factor itself or they can act as a vehicle for other cosmetic factors, known or new. In the first case two distinct possibilities present themselves:

1) the cosmetic component is based on the physical properties of the acid component of the compounds of formula (I), that of the alcoholic component being cosmetologically indifferent or 2) the main cosmetic component is the alcoholic component of the esters of formula (I).

The alcohols from which the new compounds according to alternative 1) are derived are preferably saturated aliphatic alcohols having from 1 to 8 carbon atoms, straight-chained or branched selected from the group consisting of ethyl, propyl, isopropyl, butyl, tert-butyl, hexyl and octyl alcohol. Particularly interesting are also unsaturated alcohols such as vinyl or allyl alcohols, araliphatic alcohols such as benzyl or phenethyl alcohol, and cycloaliphatic alcohols such as cyclohexyl and cyclobutyl alcohol.

With regard to alternative 2) of said new cosmetic articles, the alcohols which are used to esterify the carboxy groups are those which are themselves cosmetically or possibly therapeutically (dermatologically) active. They can be used singly or in association with other active principles that may, for example, be those contained in many essential oils and have an affinity with terpenes such as citronellol, geraniol, nerol and linalol, or the alcohols that are derived from p-menthane such as menthol, carvomenthol and terpineol, or also polyvalent alcohols such as glycerin. Dermatologically active agents are for example: antiinfective agents, antibiotics, antimicrobials, antiinflammatory agents, antivirals, anesthetics, and prophylactic agents such as sun shields, deodorants, and antiseptic and disinfectant agents. Examples of antibiotics are erythromycin, bacitracin, neomycin, aureomycin, gramicidine and their associated derivatives. Examples of antibacterials and disinfectants are nitrofurazone, mafenide, chlorexidine and derivatives of 8-hydroxyquinoline and optionally their salts. Examples of antiinflammatory agents are above all corticosteroids, such as prednisolone, dexamethasone or their esters, such as valeriantes, benzoates, and dipropionates. Examples of anesthetics are dibucane, lidocaine, and benzocaine. This list is, of course, purely for illustrative purposes and any other agent described in the literature can be used.

In the cosmetic preparations according to alternative 2), the acidic polysaccharide component essentially acts as a vehicle. Included in the present invention are also, however, cosmetic preparations in which the cosmetically active principle is simply added to a new compound of formula (I), the ester component being cosmetically active or inactive.

The compounds of formula (I) which are preferably used in cosmetics are those in which the acyl groups of the acylamino groups S are those derived from saturated aliphatic acids, substituted or unsubstituted with a maximum of 8 carbon atoms. Due to the close affinity existing between the new compounds of the invention of formula (I) and their salts, it is understood that the properties named in connection with the free-form compounds also belong to the salified compounds.

In the cosmetic articles according to the invention, the compounds of formula (I), and also said cosmetic compositions containing ingredients 1) and 2), can be mixed with the excipients commonly used in the art. Preferably, creams, ointments, and lotions for topical use are used and it is possible to add other cosmetically active principles, such as steroids, for example pregnenolone, or one of the abovenoted active ingredients thereto. The choice of acyl group which acylates the nitrogen, the percentage of the S amino groups left free or salified, the percentage of oxidation of the primary carbinolic groups, the percentage of esterification or salification, as well as the choice of esterifying group, are all variables which make it possible to modulate the characteristics of solubility, pH and viscoelasticity of the new products of formula (I).

For the manufacture of sanitary and surgical articles it is preferable to use those products of formula (I) in which the acyl group of the S acylamino groups is derived from aliphatic acids, saturated or unsaturated, straight-chained or branched, with a maximum of 8 carbon atoms, in particular acids chosen from the group formed by formic, acetic, propionic, dichloroacetic, butyric, and valerianic acids, and wherein the alcoholic component which is used to esterify the carboxy groups is chosen from the group formed by methyl, ethyl, propyl, hexyl, cyclohexyl, benzyl, phenylethyl, and vinyl alcohol.

The new products of the present invention can be used in the known way and such procedures constitute a further object of the present invention.

The procedure of the present invention for the preparation of the compounds of formula (I) comprises partially or totally esterifying, in a known way and with the desired alcohols, the carboxy groups of a compound of formula (II):

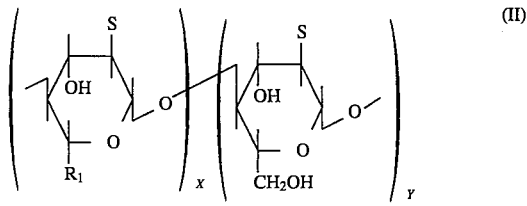

wherein the degree of polymerization, referred to the single glucoside unit, varies between the values of about 50 and 50,000, the bonds between the various glucoside units are of a $\beta(1\rightarrow 4)$ nature, $R_1$ is a carboxy group, free or salified, or esterified with an alcohol of the aliphatic, araliphatic or alicyclic series with a maximum of 26 carbon atoms, at least a part of these groups being free or salified carboxy groups, and wherein x and y indicate the percentage of the number of molecules of the respective formulae and wherein the order of succession of the single glucoside derivatives can vary. The parameter x varies between about 5% and 100%, and y varies between 95% and 0%. S is an amino or acylamino group, at least a part of the S groups being acylamino groups. The acyl moiety of the acylamino groups is derived from an acid chosen from the group formed by:

an aliphatic acid having a maximum of 26 carbon atoms an araliphatic acid with only one benzene residue and wherein the aliphatic chain has a maximum of 4 carbon atoms, and an aromatic acid with only one benzene ring, and, if desired, acylating the S amino groups thus obtained so as to obtain S acylamino groups and, also if desired, salifying the free carboxy groups in the partial ester groups obtained, and/or salifying the free amino groups.

One variant of the procedure for the preparation of compounds of the present invention comprises esterifying in a known way the carboxy groups of the oxidized chitins described in the aforesaid European patent No. 0161212, optionally after partial or complete acetylation of any free amino groups, thus obtaining products according to the present invention of formula (II) wherein S represents the acetylamino (or amino) group. Another variant comprises esterifying the carboxy groups of homologues of the oxidized chitins, wherein the N-acyl group is derived from an aliphatic acid having a maximum of 26 carbon atoms, other than acetic acid or an acid of the other aforesaid series. The starting products for said esterification are known and can be prepared in a known way. For example, the starting products wherein S is mainly N-acetyl-amino are obtained by thorough acetylation of the products described in European patent No. 0161212. The starting products wherein S is different from the acetylamino groups can be obtained by deacetylation of chitin, reacylation of the chitosan thus obtained with the desired acyl other than acetyl, and oxidation of the products thus obtained, for example, according to the procedure described in the aforesaid European patent.

Such starting substances can also be prepared by oxidation of the chitosan, for example, in a known way (see, for example, Horton, et al. Carbohydrate Research, 29, 173, 1973) and selective acylation (see, for example, Hirano, et al., Carbohydrate Research, 47, 315–320, 1976) at the amino nitrogen.

The above-said starting products can be esterified in the procedure of the present invention by treatment of the carboxy compounds in their free form with the desired alcohols in the presence of catalysts, such as strong inorganic acids or acid-type ion exchangers, or with an etherifying agent capable of introducing the desired alcohol residue in the presence of inorganic or organic bases. It is possible to use as etherifying agents those known in the literature, such as especially the esters of various inorganic acids, organic sulfonic acids, hydracids, i.e., hydrocarbyl halogenides such as methyl or ethyl iodide, hydrocarbyl neutral or acid sulfates, sulfites, carbonates, silicates, phosphites or hydrocarbyl sulfonates, such as benzene methyl sulfonate or p-toluene sulfonate, or methyl or ethyl chlorosulfonate. The reaction may proceed in a suitable solvent, for example, an alcohol, preferably that which corresponds to the alkyl group to be introduced into the carboxy group, but also in non-polar solvents, such as ketones, ethers such as dioxane or aprotic solvents such as dimethylsulfoxide. As a base, it is possible to use, for example, an alkali or alkaline earth metal hydroxide, or magnesium or silver oxide or a basic salt of one of these metals, such as a carbonate, and, of the organic bases, a tertiary azotated base such as pyridine or collidine. Instead of the base, it is possible to use a basic-type ion exchanger.

Another method of esterification makes use of metal salts or salts with organic azotated bases of the starting carboxy component, for example, ammonium or substituted ammonium salts. It is preferable to use the salts of alkali or alkaline earth metals, but any other metal salt can be used. The etherifying agents are also in this case those mentioned above and the same is true of the solvents. It is preferable to use aprotic solvents, for example, dimethylsulfoxide and dimethylformamide. In all of these standard esterification procedures commonly used, it is necessary to take care, in order to obtain substantially pure products corresponding to the compounds of formula (I), to avoid esterfication of any amino groups which may be present and therefore to choose bland (mild) conditions and thus to guarantee a selective esterification reaction. In many cases it is possible, however, to also use products corresponding to said formula (II) wherein small aliquots of amino groups may also be in an etherified form, for example, alkylated especially with lower aliphatic alcohols; such products come within the scope of the present invention. Indeed, they can be obtained in the above-described manner.

One esterification method used to obtain compounds of formula (I) which are not contaminated by products etherified to the amino groups consists in a procedure using the quaternary ammonium salts of the starting carboxy compounds. Such salts are reacted with an etherifying agent in an aprotic solvent, such as dialkylsulfoxide or dialkylcarboxylamide, and in particular, lower alkyl dialkylsulfoxides, especially dimethylsulfoxide and lower alkyl dialkylamides of lower aliphatic acids, such as dimethyl or diethyl formamide or dimethyl or diethyl acetamide. The reaction is effected preferably in a temperature range of between about 0° and 100° C. and especially between about 25° and 75° C., for example, at about 30° C. Esterification is performed preferably by gradually adding the esterifying agent in substantially equimolecular quantities to the abovesaid ammonium salt dissolved in one of the aforesaid solvents, for example, dimethylsulfoxide.

As alkylating agents, it is possible to use those mentioned above, especially hydrocarbyl halogenides, for example, alkyl halogenides. As starting quaternary ammonium salts, it is preferable to use lower ammonium tetraalkylates, the alkyl groups having preferably from one to six carbon atoms. Mainly, the tetrabutylammonium salt is used. These quaternary ammonium salts can be prepared by reacting a metal salt of the compound of formula (II), preferably one of those mentioned above, particularly the sodium or potassium salt, in an aqueous solution with a sulfonic resin salified with the quaternary ammonium base. The tetraalkylammonium salt can be obtained by freeze-drying the eluate. The tetraalkylammonium salts derived from lower alkyl groups, especially alkyls having 1 to 6 carbon atoms, are new and form another object of the present invention. Such salts are soluble in said aprotic solvents, and thus the esterification of the compounds of formula (II), according to said procedure, is particularly convenient and gives quantitative yields. It is therefore only by using a procedure of this kind that one can exactly regulate the number of carboxy groups of the compounds of formula (II) to be esterified.

One variant of the previously specified procedure comprises reacting the potassium, sodium or cesium salt of the compounds of formula (II) suspended in a suitable aprotic solvent such as dimethylsulfoxide, with a suitable alkylating agent, in the presence of catalyzing quantities of a quaternary ammonium salt, such as tetrabutylammonium iodide. The aforesaid optional acylation can be effected by known methods. It is best to use the selective methods described above.

In the esters obtained according to such procedures, possible free carboxy groups of partial esters can be salified, if desired, in a known way. In the partial esters of the present invention, it is possible to salify all of the remaining carboxy groups or only part of these, by regulating the basic quantities so as to obtain the desired stoichiometric degree of salification. By suitably selecting the degree of salification, it is possible to obtain esters with a wide range of different dissociation constants, thus providing the desired pH in solution or "in situ". Lastly, in all the compounds obtainable according to the aforesaid procedures which present salifiable groups, such groups can be salified according to procedures known in the art.

The following examples are given merely as illustrative of the present invention and are not to be considered as limiting.

EXAMPLE 1

Ethyl ester of oxidized N-acetyl-chitosan

Degree of nitrogen substitution=1

Degree of oxidation=0.54

Degree of esterification=1

The N-acetyl-chitosan (degree of nitrogen substitution=1) is prepared according to the procedure of Hirano, et al., Carbohydrate Research, 47, 315–320 (1976). Oxidation of the N-acetyl-chitosan is performed using nitrogen dioxide and following the method described in the paper by Yackel, et al. J. Am. Chem. Soc., 64 121–131 (1942).

An oxidized N-acetyl-chitosan with a degree of nitrogen substitution=1 and a degree of oxidation=0.54 is thus obtained.

3.9 g of oxidized N-acetyl-chitosan with a degree of substitution of 0.54 are suspended in 300 ml of distilled $H_2O$ and neutralized with a 1N solution of NaOH to pH 7.0. The solution is then eluted in a thermostatic column set at 4° C. containing 15 ml of sulfonic resin (Dowex 50×8) generated in the form of tetrabutylammonium. The sodium-free eluate is instantly frozen and freeze-dried. 6.2 g of the tetrabutylammonium salt of oxidized N-acetyl-chitosan are thus obtained.

6.2 g of the previously prepared tetrabutylammonium salt are solubilized in 300 ml of constantly stirred N-methylpyrrolidone at 25° C. 1.56 g of ethyl iodide are added. The solution is stirred overnight at 30° C. and then precipitated in 1500 ml of ethyl acetate. The precipitate is separated by filtration, washed three times with 100 ml of ethyl acetate and then dried. 4.05 g of the title product are thus obtained. Quantitative determination of the ester groups is performed according to the saponification method described on pages 169–172 of "Quantitative Organic Analysis via Functional Groups", 4th Edition, John Wiley and Sons.

EXAMPLE 2

Ethyl ester of oxidized N-acetyl-chitosan

Degree of nitrogen substitution=1

Degree of oxidation=0.99

Degree of esterification=1

The chitosan is oxidized with $Cro_3$ as described in the paper by Horton, et al., Carbohydrate Research, 29, 173–179 (1973).

To 2 g of the oxidized chitosan are added 40 ml of water, 4 ml of methanol, 3 ml of acetic anhydride and 35 ml of Dowex 1, carbonate form, anion-exchange resin. The solution is kept at 0°–4° C. for 3 hours. When the resin has been removed by filtration, the solution is concentrated to about 15 ml. 50 ml of ethanol are added. The resulting precipitate is gathered by centrifugation and dissolved in water. The solution is passed through an acid form Amberlite J R-120 column. The eluates are neutralized to pH 8.5 and vacuum-concentrated to 40 ml. By adding ethanol a precipitate is obtained which is filtered. 1.0 g of oxidized N-acetyl-chitosan are thus obtained, with a degree of nitrogen substitution=1 and a degree of oxidation=0.99.

Esterification is performed as described in Example 1 through the tetrabutylammonium salt. 0.95 g of the title product are thus obtained.

Quantitative determination of the ester groups is performed according to the saponification method described on pages 169–172 of "Quantitative organic Analysis via Functional Groups", 4th Edition, John Wiley and Sons.

EXAMPLE 3

Benzyl ester of oxidized N-acetyl-chitosan

Degree of nitrogen substitution=1

Degree of oxidation=0.54

Degree of esterification=1

The tetrabutylammonium salt of oxidized N-acetyl-chitosan is prepared as described in Example 1. 6.32 g of the tetrabutylammonium salt of oxidized N-acetyl-chitosan are solubilized in 300 ml of constantly stirred pure N-acetylpyrrolidone at 25° C. 1.71 g of benzyl bromide are added. The solution is stirred overnight at 30° C. and then precipitated in 1500 ml of ethyl acetate. The precipitate is separated by filtration, washed three times with 100 ml of pure ethyl acetate and then dried. 4.6 g of the title product are thus obtained.

Quantitative determination of the ester groups is performed according to the saponification method described on pages 169–172 of "Quantitative Organic Analysis via Functional Groups" 4th Edition, John Wiley and Sons.

EXAMPLE 4 n-propyl ester of oxidized N-acetyl-chitosan

Degree of nitrogen substitution=1

Degree of oxidation=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 g of the tetrabutylammonium salt of oxidized N-acetyl-chitosan are solubilized in 300 ml of constantly stirred N-acetylpyrrolidone at 25° C. 1.7 g of n-propyl iodide are added. The solution is stirred overnight at 30° C. and then precipitated in 1500 ml of ethyl acetate. The precipitate is separated by filtration, washed three times with 100 ml of pure ethyl acetate and then dried. 6.4 g of the title product are thus obtained.

Quantitative determination of the ester groups is performed according to the saponification method described on pages 169–172 of "Quantitative Organic Analysis via Functional Groups" 4th Edition, John Wiley and Sons.

EXAMPLE 5 n-pentyl ester of oxidized N-acetyl-chitosan

Degree of nitrogen substitution=1

Degree of oxidization=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 g of the tetrabutylammonium salt of oxidized N-acetyl-chitosan are solubilized in 300 ml of constantly stirred N-methylpyrrolidone at 25° C. 1.98 g of 1-iodo-pentane are added. The solution is stirred overnight at 30° C. and then precipitated in 1500 ml of ethyl acetate. The precipitate is separated by filtration, washed three times with 100 ml of pure ethyl acetate and then dried. 6.9 g of the title product are thus obtained.

Quantitative determination of the ester groups is performed according to the saponification method described on pages 169–172 of "Quantitative Organic Analysis via Functional Groups" 4th Edition, John Wiley and Sons.

EXAMPLE 6

2-fluoro-benzyl ester of oxidized N-acetyl-chitosan

Degree of nitrogen substitution=1

Degree of oxidation=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 of the tetrabutylammonium salt of oxidized N-acetyl-chitosan are solubilized in 300 ml of constantly stirred N-methylpyrrolidone at 25° C. 1.89 g of 2-fluorobenzyl bromide are added. The solution is stirred overnight at 30° C. and then precipitated in 1500 ml of ethyl acetate. The precipitate is separated by filtration, washed three times with 100 ml of pure ethyl acetate and then dried. 7.25 g of the title product are thus obtained.

Quantitative determination of the ester groups is performed according to the saponification method described on pages 169–172 of "Quantitative organic Analysis via Functional Groups", 4th Edition, John Wiley and Sons.

EXAMPLE 7

2-chloro-benzyl ester of oxidized N-acetyl-chitosan

Degree of nitrogen substitution=1

Degree of oxidation=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 g of the tetrabutylammonium salt of oxidized N-acetyl-chitosan are solubilized in 300 ml of constantly stirred N-methylpyrrolidone at 25° C. 2.06 g of 2-chlorobenzyl bromide are added. The solution is stirred overnight at 30° C. and then precipitated in 1500 ml of ethyl acetate. The precipitate is separated by filtration, washed three times with 100 ml of pure ethyl acetate and then dried. 7.0 g of the title product are thus obtained.

Quantitative determination of the ester groups is performed according to the saponification method described on pages 169–172 of "Quantitative Organic Analysis via Functional Groups", 4th Edition, John Wiley and Sons.

EXAMPLE 8

5 Dodecyl ester of oxidized N-acetyl-chitosan

Degree of nitrogen substitution=1

Degree of oxidation=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 of the tetrabutylammonium salt of oxidized N-acetyl-chitosan are solubilized in 300 ml of constantly stirred N-methylpyrrolidone at 25° C. 2.49 g of dodecyl bromide are added. The solution is stirred overnight at 30° C. and then precipitated in 1500 ml of ethyl acetate. The precipitate is separated by filtration, washed three times with 100 ml of pure ethyl acetate and then dried. 7.8 g of the title product are thus obtained.

Quantitative determination of the ester groups is performed according to the saponification method described on pages 169–172 of "Quantitative Organic Analysis via Functional Groups", 4th Edition, John Wiley and Sons.

EXAMPLE 9

Isopropyl ester of oxidized N-acetyl-chitosan

Degree of nitrogen substitution=1

Degree of oxidation=0.33

Degree of esterification=1

The tetrabutylammonium salt of oxidized N-acetyl-chitosan is prepared as described in Example 1 (except for the quantity of $N_2O_4$, which in this case is less, to limit the degree of oxidation). 8.65 g of the tetrabutylammonium salt of oxidized N-acetyl-chitosan are solubilized in 300 ml of constantly stirred N-methylpyrrolidone at 25° C. 1.7 g of isopropyl iodide are added. The solution is stirred overnight at 30° C. and then precipitated in 1500 ml of ethyl acetate. The precipitate is separated by filtration, washed three times with 100 ml of pure ethyl acetate and then dried. 6.5 g of the title product are thus obtained.

Quantitative determination of the ester groups is performed according to the saponification method described on pages 169–172 of "Quantitative Organic Analysis via Functional Groups", 4th Edition, John Wiley and Sons.

EXAMPLE 10

Ethyl ester of oxidized N-propionyl-chitosan

Degree of nitrogen substitution=1

Degree of oxidation=0.5

Degree of esterification=1

N-propionyl-chitosan (degree of nitrogen substitution=1) is prepared according to the procedure of Hirano, et al., Carbohydrate Research, 47, 315–320 (1976). Oxidation of the N-propionyl-chitosan is performed using nitrogen dioxide and following the method described in the paper by Yackel, et al., J. Am. Chem. Soc., 64, 121–131 (1942). Oxidized N-propionyl-chitosan with a degree of nitrogen substitution=1 and a degree of oxidation=0.5 is thus obtained.

3.5 g of oxidized N-propionyl-chitosan having a degree of substitution of 0.5 are suspended in 300 ml of distilled water and neutralized with a 1N solution of NaOH to pH 7.0. The solution is then eluted in a thermostatic column set at 4° C. containing 15 ml of sulfonic resin (Dowex 50×8) generated in the tetrabutylammonium form. The sodium-free eluate is instantly frozen and freeze-dried. 5.5 g of the tetrabutylammonium salt of oxidized N-propionyl-chitosan are obtained.

5.5 g of the previously prepared tetrabutylammonium salt are solubilized in 300 ml of N-methylpyrrolidone at 25° C. while being stirred. 1.5 g of ethyl iodide are added. The solution is stirred overnight at 30° C. and then precipitated in 1500 ml of ethyl acetate. The precipitate is separated by filtration, washed three times with 100 ml of ethyl acetate and then dried. 3 g of the title product are thus obtained.

Quantitative determination of the ester groups is performed according to the saponification method described on pages 169–172 of "Quantitative Organic Analysis via Functional Groups", 4th Edition, John Wiley and Sons.

The following is claimed:

1. A copolymer of the formula:

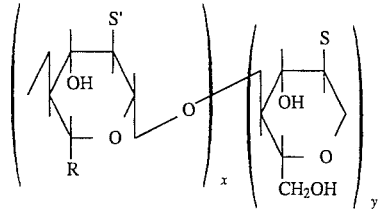

wherein the bonds are β (1→4) between the glucoside units, the degree of polymerization referred to a single glucoside unit varies within a range of about 50 to 50,000, R is a free carboxy group or a carboxy group esterified with an alcohol of the aliphatic, araliphatic or alicyclic series having a maximum of 26 carbon atoms and S represents an amino or acylamino group, wherein the acyl group is derived from an acid selected from the group consisting of:

an aliphatic acid having a maximum of 26 carbon atoms, an araliphatic acid with only one benzene residue and wherein the aliphatic chain has a maximum of 4 carbon atoms and an aromatic acid with only one benzene ring, and wherein x and y indicate the percentage of the number of molecules of the respective formulae, and wherein the order of succession of the single glucoside derivatives may also vary, x varying between about 20% and 90% and y varying between about 80% and 10%, at least a part of the R groups being esterified carboxy groups, and at least a part of the S groups being acylamino groups, and salts thereof, said salts being metal salts or organic base salts at the carboxy groups, or salts obtained by addition of acids to the free amino groups.

2. A copolymer or a salt thereof according to claim 1, wherein the aliphatic alcohol has a maximum of 12 carbon atoms and is unsubstituted or substituted by one or more free or functionally modified groups selected from the group consisting of halogens, amino groups and hydroxy groups.

3. A copolymer or a salt thereof according to claim 2, wherein the aliphatic alcohol has a maximum of 4 carbon atoms.

4. A copolymer or a salt thereof according to claim 1, wherein the araliphatic alcohol has one benzene residue and the aliphatic chain has a maximum of 4 carbon atoms, and wherein the benzene residue can be substituted by from 1 to 3 methyl or hydroxy groups or by halogen atoms, or the aliphatic chain can be substituted by one or two free or mono- or diethylated amino groups.

5. A copolymer or a salt thereof according to claim 1, wherein the alicyclic alcohol is a mono- or polycyclic hydrocarbon having a maximum of 20 carbon atoms.

6. A copolymer or a salt thereof according to claim 5, wherein the alcohol is monocyclic with a maximum of 12 carbon atoms and the ring has from 5 to 7 carbon atoms optionally substituted by 1 to 3 lower alkyl groups.

7. A copolymer or a salt thereof according to claim 1, wherein at least a part of the S groups comprises acylamino groups wherein the acyl group is derived from phenoxyacetic acid.

8. A copolymer or a salt thereof according to claim 1, wherein 100% of the S groups are acylamino groups.

9. A copolymer or a salt thereof according to claim 1, wherein from 95% to 25% of the S groups are constituted by acylamino groups.

10. A copolymer or a salt thereof according to claim 1, wherein the degree of polymerization falls within a range of about 240 to about 2400.

11. A copolymer or a salt thereof according to claim 1, wherein x corresponds to a percentage varying between 50% and 90%.

12. A copolymer or a salt thereof according to claim 1, wherein between 50% and 80% of the carboxy groups are esterified.

13. An alkali or alkaline earth metal or an aluminum, ammonium or magnesium salt of a copolymer according to claim 1.

14. A sodium or ammonium salt of a copolymer according to claim 1.

15. An amine salt of a copolymer according to claim 1, wherein the amine is a therapeutically acceptable base.

16. An acid addition salt of a copolymer according to claim 1, wherein the acid is a therapeutically acceptable acid.

17. A copolymer or a salt thereof according to claim 1, wherein part of the S groups are constituted by acetamino groups.

18. A copolymer or a salt thereof according to claim 1, wherein the carboxy groups are esterified, and wherein the alcohol used for esterification is a cosmetically effective alcohol.

19. A copolymer or a salt thereof according to claim 1, wherein the carboxy groups are esterified, and wherein the alcohol used for esterification is a therapeutically active alcohol.

20. A cosmetic composition which comprises the copolymer or salt of claim 18, and a cosmetically acceptable excipient.

21. A cosmetic composition which comprises the copolymer or salt of claim 19, and a cosmetically acceptable excipient.

22. A copolymer or a salt thereof according to claim 1, wherein said copolymer or salt thereof is in the form of a film, a sheet, a suture thread for surgery, gauze, or tissue.

23. A sanitary or surgical article containing a copolymer or a salt thereof according to claim 1.

24. A sanitary or surgical article according to claim 23, wherein said article is a heart valve, an intraocular lens, a vascular clip or a pacemaker.

25. A cosmetic article containing a copolymer or a salt thereof according to claim 1.

26. The cosmetic article according to claim 25, which is a cream, ointment, or lotion for topical use.

* * * * *